United States Patent
Kawashima et al.

(10) Patent No.: US 7,141,579 B2
(45) Date of Patent: Nov. 28, 2006

(54) HETEROCYCLIC COMPOUNDS AND CEREBRAL FUNCTION IMPROVERS CONTAINING THE SAME AS THE ACTIVE INGREDIENT

(75) Inventors: Seiichiro Kawashima, Tokyo (JP); Toshiyuki Matsuno, Tokyo (JP); Naoki Fukuda, Tokyo (JP); Kenichi Saitoh, Tokyo (JP); Yoshimasa Yamaguchi, Tokyo (JP); Masaya Higashi, Tokyo (JP)

(73) Assignee: Zenyaku Kogyo Kabushiki Kaisha, Tokyo (JP)

( * ) Notice: Subject to any disclaimer, the term of this patent is extended or adjusted under 35 U.S.C. 154(b) by 91 days.

(21) Appl. No.: 10/466,321

(22) PCT Filed: Jan. 30, 2002

(86) PCT No.: PCT/JP02/00694

§ 371 (c)(1),
(2), (4) Date: Jul. 29, 2003

(87) PCT Pub. No.: WO02/060907

PCT Pub. Date: Aug. 8, 2002

(65) Prior Publication Data

US 2004/0048879 A1     Mar. 11, 2004

(30) Foreign Application Priority Data

Jan. 30, 2001    (JP)  ............................. 2001-022385

(51) Int. Cl.
     *A61K 31/44*      (2006.01)
     *C07D 471/04*     (2006.01)
     *C07D 471/10*     (2006.01)

(52) U.S. Cl. ..................... 514/300; 546/121
(58) Field of Classification Search ............... 546/121; 514/300
See application file for complete search history.

(56) References Cited

U.S. PATENT DOCUMENTS

| 5,721,223 A | 2/1998 | Hansen, Jr. et al. |
| 6,114,334 A | 9/2000 | Kerrigan et al. |
| 6,635,652 B1 | 10/2003 | Kawashima et al. |

FOREIGN PATENT DOCUMENTS

| EP | 0 524 055 | 1/1993 |
| EP | 703233 | 3/1996 |
| JP | 63-141969 | 6/1988 |
| JP | 63-145286 | 6/1988 |

OTHER PUBLICATIONS

M. E. Baumann, et al., Helvetica Chimica Acta, vol. 69, No. 2, pp. 396-403, XP-001098393, "Herstellung von Disubstituierten Maleinsäure-Anhydriden mit Hilfe von Reaktiven 2-Oxo-3*H*-Imidazo [1,2-a]Pyridinium-Verbindungen", Mar. 19, 1986.

*Primary Examiner*—Rita Desai
(74) *Attorney, Agent, or Firm*—Oblon, Spivak, McClelland, Maier & Neustadt, P.C.

(57) ABSTRACT

Heterocyclic compound represented by the formula I

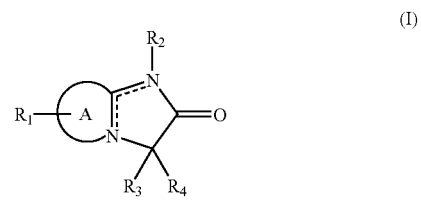

(I)

wherein

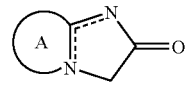

represents

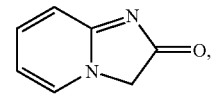

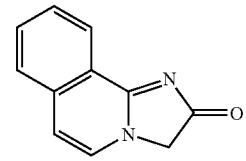

or the like; $R_1$ represents hydrogen atom, $C_1$–$C_6$ alkyl or benzyloxy; $R_2$ represents methyl or nil; $R_3$ represents hydrogen atom, $C_1$–$C_6$ alkyl, $C_2$–$C_6$ alkenyl, $C_3$–$C_8$ cycloalkyl or —$CH_2R_5$ [wherein $R_5$ represents phenyl (which may be substituted with $C_1$–$C_6$ alkyl, halogen atom or cyano)] or thienyl; $R_4$ represents $C_1$–$C_6$ alkyl, $C_2$–$C_6$ alkenyl, $C_3$–$C_8$ cycloalkyl or —$CH_2R_6$ [wherein $R_6$ represents phenyl (which may be substituted with $C_1$–$C_6$ alkyl, halogen atom or cyano), naphthyl or thienyl]; or $R_3$ is coupled with $R_4$.

15 Claims, No Drawings

HETEROCYCLIC COMPOUNDS AND CEREBRAL FUNCTION IMPROVERS CONTAINING THE SAME AS THE ACTIVE INGREDIENT

TECHNICAL FIELD

The present invention relates to heterocyclic compounds and cognitive enhancers comprising the compounds as effective components, represented by the formula I

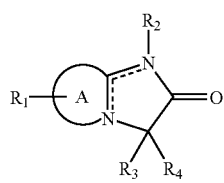
(I)

wherein

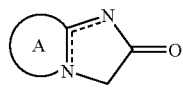

represents

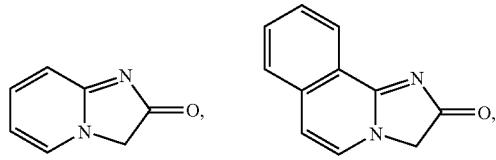

$R_1$ represents hydrogen atom, $C_1$–$C_6$ alkyl or benzyloxy; $R_2$ represents methyl or nil; $R_3$ represents hydrogen atom or $C_1$–$C_6$ alkyl, $C_2$–$C_6$ alkenyl, $C_3$–$C_8$ cycloalkyl or —$CH_2R_5$ [wherein $R_5$ represents phenyl (which may be substituted with $C_1$–$C_6$ alkyl, halogen atom or cyano) or thienyl]; $R_4$ represents $C_1$–$C_6$ alkyl, $C_2$–$C_6$ alkenyl, $C_3$–$C_8$ cycloalkyl or —$CH_2R_6$ [wherein $R_6$ represents phenyl (which may be substituted with $C_1$–$C_6$ alkyl, halogen atom or cyano), naphtyl or thienyl]; or $R_3$ is coupled with $R_4$ into

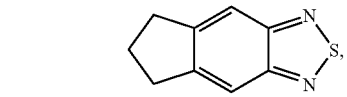

(wherein $R_7$ represents hydrogen atom, halogen atom, $C_1$–$C_6$ alkoxy, cyano or trifluoromethyl),

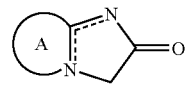

cyclopentene or cyclopentane, provided that, when

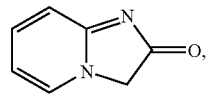

represents

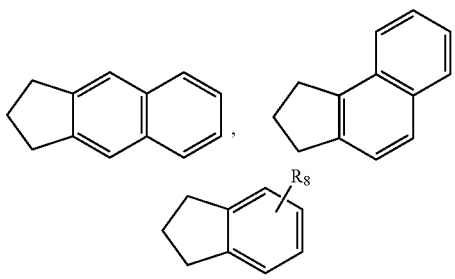

$R_3$ is a hydrogen atom or is coupled with $R_4$ into

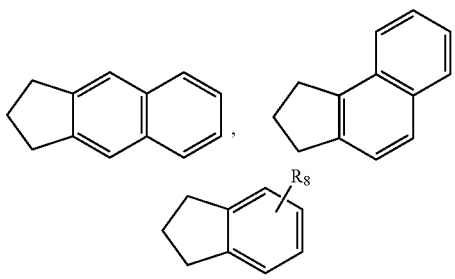

(wherein $R_8$ represents halogen atom, $C_1$–$C_6$ alkoxy, cyano or trifluoromethyl),

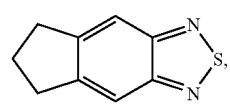

cyclopentene or cyclopentane and that, only when represents

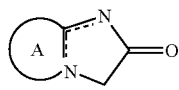

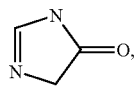

$R_2$ exists as a substituent and may be methyl.

More specifically, it relates to heterocyclic compounds useful as cognitive enhancers in connection with treatments on memory disturbance, memory acquirement and retention disturbance in, for example, senile dementia and Alzheimer's disease.

BACKGROUND ART

In recent years and with prolongation in average life span, diseases such as senile dementia with memory disturbance are causing medically and socially great problems.

Dementia is a condition that cerebral functions once developed have been continually retarded as regard to memory, cognition and thinking, resulting in problems in ordinary social life. Alzheimer's disease, cerebrovascular dementia and mixture thereof amount to eight- or nine-tenths of underlying diseases for senile dementia, a core symptom of which is memory impairment. Known with respect to Alzheimer's disease are the facts that the activity of choline acetyltransferase (ChAT), which is an acetylcholine sythesizing enzyme in the cerebral cortex, is lowered in comparison with normal control group of the same age [Bowen et al., Brain, 99, 459 (1976)] and that neurons in the nucleus basalis of Meynert, which is the nuclei of origin in cholinergic nerve of the cerebral cortex, are eminently exfoliated [Whitehouse et al., Science, 215, 1237–1239 (1982)]. Moreover, it is known, for example, that retarded cognitive function in terms of mental test score is related with lowered ChAT activity of the cerebral cortex [Perry et al., Br. Med. J. 25, 1457–1459 (1978)] and that scopolamine, which is a pharmacologically muscarinic receptor antagonist, causes amnesia [Drachman, Neurology, 27, 783–790 (1977)]. Set up against these backgrounds was a cholinergic hypothesis to the effect that memory is deeply linked with cholinergic nerve [Bartus et al., Science, 217, 408–417 (1982)]; nowadays, approaches based on cholinergic hypothesis have been made on development of curative medicines for senile dementia. Especially, experimental animal models with learning and memory disturbance induced by anti-cholinergic chemicals (e.g., scopolamine) have been widely utilized in quest of medicines effective for learning and memory disturbance due to generally various causes of diseases (e.g., senile dementia including Alzheimer's disease).

Development of curative medicines effective against senile dementia has been strongly demanded; up to the present, antidementia medicines such as linopirdine, tacrine or aricept have been proposed and some of them have been marketed.

However, none of developed and marketed antidementia medicines are satisfactory in improvement and remedy of dementia symptoms. There are still, therefore, strong demands on development of more effective antidementia medicines.

DISCLOSURE OF THE INVENTION

We, the inventors, have devoted researches to pursue compounds having effectiveness against cognitive dysfunction in the central nervous system, especially cholinergic nervous system, and found heterocyclic compounds of the formula I having significant anti-amnesic effects against scopolamine-induced amnesia of rats, thus accomplishing the present invention.

The compounds of the present invention are represented by the formula I. The terms used for definition of letters in the formula will be defined and exemplified in the following.

The term "$C_1$–$C_6$" refers to a group having 1 to 6 carbon atoms unless otherwise indicated.

The term "$C_2$–$C_6$" refers to a group having 2 to 6 carbon atoms unless otherwise indicated.

The term "$C_3$–$C_8$" refers to a group having 3 to 8 carbon atoms unless otherwise indicated.

The "$C_1$–$C_6$ alkyl" refers to a straight- or branched-chain alkyl group such as methyl, ethyl, n-propyl, isopropyl, n-butyl, tert-butyl, sec-butyl, n-pentyl or n-hexyl.

The "$C_3$–$C_8$ cycloalkyl" refers to cyclopropyl, cyclobutyl, cyclopentyl, cyclohexyl, cycloheptyl, cyclooctyl.

The "$C_2$–$C_6$ alkenyl" refers to a straight- or branched-chain alkenyl group such as vinyl, propenyl, isopropenyl, butenyl, pentenyl or hexenyl.

The "$C_1$–$C_6$ alkoxy" refers to a straight- or branched-chain alkoxy group such as methoxy, ethoxy, n-propoxy, isopropoxy, n-butoxy, tert-butoxy, sec-butoxy, n-pentyloxy, n-hexyloxy.

The "halogen atom" refers to fluorine, chlorine, bromine or iodine atom.

The compounds of the present invention may be as follows, though the present invention is not limited to these compounds.

spiro[imidazo[2,1-b]thiazol-6(5H)-one-5,2'-benzo[f]-indan]
spiro[imidazo[1,2-b]thiazol-6(5H)-one-5,2'-indan]
spiro[2-methylimidazo[1,2-b]thiazol-6(5H)-one-5,2'-benzo[f]indan]
5,5-bis(4-fluorobenzyl)imidazo[2,1-b]thiazol-6(5H)-one
5,5-dibenzylimidazo[2,1-b]thiazol-6(5H)-one
5,5-bis(4-methylbenzyl)imidazo[2,1-b]thiazol-6(5H)-one
5,5-bis(4-cyanobenzyl)imidazo[2,1-b]thiazol-6(5H)-one
5,5-dibenzyl-2-methylimidazo[2,1-b]thiazol-6(5H)-one
5,5-bis(4-fluorobenzyl)-2-methylimidazo[2,1-b]-thiazol-6(5H)-one
5,5-dicyclohexyl-2-methylimidazo[2,1-b]thiazol-6(5H)-one
5,5-bis(4-cyanobenzyl)-2-methylimidazo[2,1-b]thiazol-6(5H)-one
5,5-di(2-butenyl)imidazo[2,1-b]thiazol-6(5H)-one
5,5-dibutylimidazo[2,1-b]thiazol-6(5H)-one
5,5-dicyclohexylimidazo[2,1-b]thiazol-6(5H)-one
5,5-bis(2-thienylmethyl)imidazo[2,1-b]thiazol-6(5H)-one
spiro[2,3-dihydroimidazo[2,1-b]thiazol-6(5H)-one-5,2'-benzo[f]indan]
5,5-dibutyl-2,3-dihydroimidazo[2,1-b]thiazol-6(5H)-one
5,5-di(2-butenyl)-2,3-dihydroimidazo[2,1-b]thiazol-6(5H)-one
5,5-bis(4-methylbenzyl)-2,3-dihydroimidazo[2,1-b]-thiazol-6(5H)-one
5,5-bis(2-thienylmethyl)-2,3-dihydroimidazo[2,1-b]-thiazol-6(5H)-one 5,5-bis(4-fluorobenzyl)-2,3-dihydroimidazo[2,1-b]-thiazol-6(5H)-one
5,5-dibenzyl-2,3-dihydroimidazo[2,1-b]thiazol-6(5H)-one
spiro[imidazo[1,2-a]pyridin-2(3H)-one-3,2'-benzo[f]-indan]
2-hydroxy-3-(2-naphthylmethyl)-imidazo[1,2-a]pyridine
3-benzylimidazo[1,2-a]pyridin-2(3H)-one
spiro[5,6,7,8-tetrahydroimidazo[1,2-a]pyridin-2(3H)-one-3, 2'-benzo[f]indan]
3,3-dicyclohexyl-5,6,7,8-tetrahydroimidazo[1,2-a]-pyridin-2(3H)-one
3,3-bis(2-thienylmethyl)-5,6,7,8-tetrahydroimidazo-[1,2-a]pyridin-2(3H)-one
3,3-dibutyl-5,6,7,8-tetrahydroimidazo[1,2-a]pyridin-2(3H)-one
3,3-dipropyl-5,6,7,8-tetrahydroimidazo[1,2-a]pyridin-2(3H)-one
spiro[imidazo[1,2-a]pyrimidin-2(3H)-one-3,2¹-benzo[f]-indan]
3,3-di(2-butenyl)imidazo[1,2-a]pyrimidin-2(3H)-one
3,3-bis(2-thienylmethyl)imidazo[1,2-a]pyrimidin-2(3H)-one
3,3-bis(4-fluorobenzyl)imidazo[1,2-a]pyrimidin-2(3H)-one
3,3-dicyclohexylimidazo[1,2-a]pyrimidin-2(3H)-one
3,3-bis(4-cyanobenzyl)imidazo[1,2-a]pyrimidin-2(3H)-one
3,3-bis(4-methylbenzyl)imidazo[1,2-a]pyrimidin-2(3H)-one
4,4-dibenzyl-1-methyl-5-oxo-4,5-dihydroimidazole
spiro[imidazo[1,2-a]pyridin-2(3H)-one-3,2'-(4'-fluoroindan)]
spiro[imidazo[1,2-a]pyridin-2(3H)-one-3,2'-(5'-methoxyindan)]
spiro[imidazo[1,2-a]pyridin-2(3H)-one-3,2'-(5-iodoindan)]
spiro[imidazo[1,2-a]pyridin-2(3H)-one-3,2'-(4'-cyanoindan)]
spiro[imidazo[2,1-a]isoquinolin-2(3H)-one-3,2'-indan]
spiro[imidazo[1,2-a]pyridin-2(3H)-one-3,2'-((1,2,5-thiadiazo)[4,5-c]indan]
spiro[imidazo[2,1-a]isoquinolin-2(3H)-one-3,2'-((1,2,5-thiadiazo)[4,5-c]indan)]
spiro[imidazo[1,2-a]pyrimidin-2(3H)-one-3,1'-(3'-cyclopentene)]
spiro[imidazo[1,2-a]primidin-2(3H)-one-3,2'-indan]
spiro[imidazo[1,2-a]primidin-2(3H)-one-3,2'-((1,2,5-thiadiazo)[4,5-c]indan)]
spiro[imidazo[1,2-a]pyridin-2(3H)-one-3,2'-(5'-trifluoromethylindan)]
spiro[imidazo[1,2-a]pyridin-2(3H)-one-3,2'-benzo[e]-indan]
spiro[imidazo[2,1-a]isoquinolin-2(3H)-one-3,1'-(3'-cyclopentene)]
spiro[8-benzyloxyimidazo[1,2-a]pyridin-2(3H)-one-3,1'-(3'-cyclopentene)]
spiro[7,8,9,10-tetrahydroimidazo[2,1-a]isoquinolin-2(3H)-one-3,1'-cyclopentane]
spiro[imidazo[2,1-a]isoquinolin-2(3H)-one-3,1'-cyclopentane]
spiro[5,6,7,8-tetrahydroimidazo[1,2-a]pyridin-2(3H)-one-3,2'-indan]

The compounds I of the present invention may have asymmetric carbon atoms in its structure. It is to be understood that isomers due to such asymmetric carbon atom or combination (racemate) of any of the isomers are included in the category of the compounds according to the present invention.

Moreover, the compound I of the present invention may exist in the form of tautomers as shown in the following formula when $R_3$ is hydrogen atom. It is to be understood that all of these tautomers are included in the category of the compounds according to the present invention.

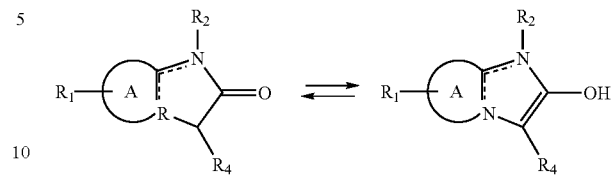

wherein the basic structure

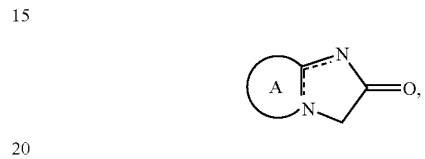

$R_1$, $R_2$ and $R_4$ are as defined above.

[Production Processes]

The compounds of the present invention represented by the formula I are novel compounds and may be prepared in application of method of Kakei et al. [Bulletin Chemical Society Japan, vol. 55, No. 11, 3590–3597 (1982)]. More specifically, the compounds I according to the present invention except those with

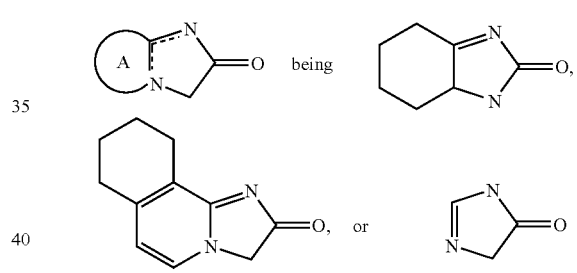

are produced as shown in the following reaction formula; quaternary salt represented by the formula II as starting material is reacted with halide represented by the formula III or III' under the presence of base such as 1,8-diazabicyclo[5, 4, 0]-7-undecene, sodium ethoxide or sodium hydroxide.

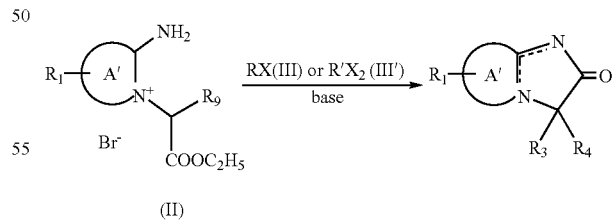

wherein $R_1$, $R_3$ and $R_4$ are as defined above and

represents

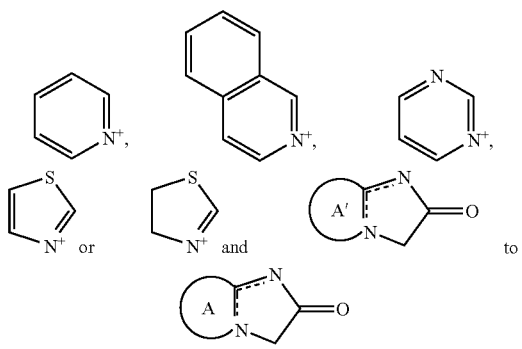

is as defined above with respect except that

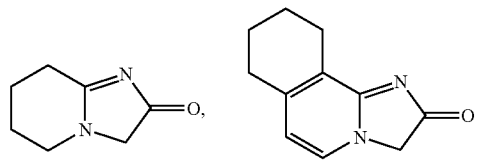

and

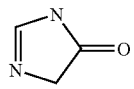

are excluded; $R_9$ represents a hydrogen atom, $C_1$–$C_6$ alkyl, $C_2$–$C_6$ alkenyl, $C_3$–$C_8$ cycloalkyl or —$CH_2R_6$ (wherein $R_6$ is as defined above); R represents $C_1$–$C_6$ alkyl, $C_3$–$C_8$ cycloalkyl or —$CH_2R_6$ (wherein $R_6$ is as defined above); R' represents

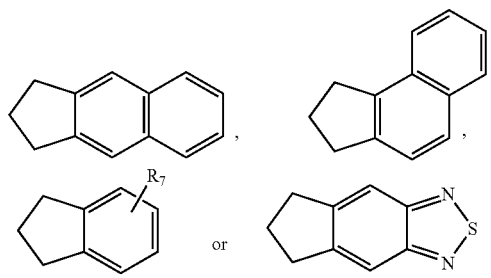

(wherein $R_7$ is as defined above); and X represents chlorine atom or bromine atom.

In this reaction, per mole of the compound II, 2.0–2.2 moles of the compound III or 1.0–1.2 moles of the compound III', and 2–4 moles of the base are used when $R_9$ is hydrogen atom; and 1.0–1.2 moles of the compound III and 1–2 moles of the base are used when $R_9$ is not hydrogen atom. The reaction is made in the solvent at the temperature of 0–50° C. for 2–50 hours.

The solvent employed may be dimethylformamide (DMF), tetrahydrofuran (THF), acetonitrile, methanol or ethanol.

The compound of the present invention having cyclopentene formed by $R_3$ and $R_4$ can be produced by carrying out ring formation reaction under the presence of Grubbs reagent, using the compounds produced in the above-mentioned production process with both of $R_3$ and $R_4$ being allyl group.

In this case, 0.05–0.5 mole of Grubbs reagent is used per mol of the above-mentioned diallyl compound and the reaction is made in a solvent at a temperature range from room temperature to 150° C. for 5–50 hours. The solvent used may be dioxane, toluene, chloroform, dichloromethane or THF.

The compounds I of the present invention wherein

represents

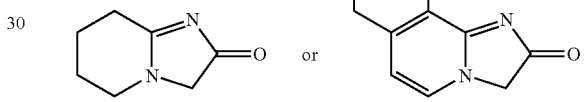

or $R_3$ is coupled with $R_4$ into cyclopentane can be produced by carrying out catalytic reduction by a normal method under hydrogen atmosphere in the presence of palladium carbon as catalyst, using the compounds of the present invention obtained in the above-mentioned production process wherein

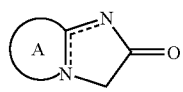

represents

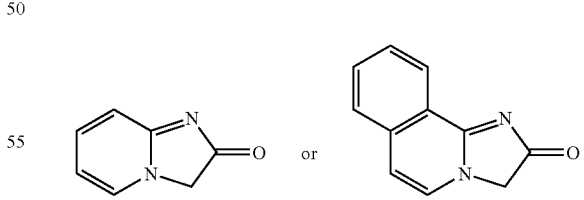

or $R_3$ is coupled with $R_4$ into cyclopentene.

In this case, the amount of the catalyst used may range from one-tenth to the same amount of that of the starting material and one-fifth is preferable. The reaction solvent used may be ethanol, methanol or chloroform and ethanol is preferable. The reaction is made in a temperature of 0–50° C. and the preferable reaction temperature is room temperature.

The compounds I of the present invention wherein

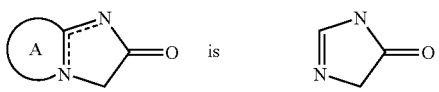

can be obtained by reacting isocyano ethylacetate with methylamine; the obtained isocyano acetamide is reacted with the above-mentioned compound III or III' in the presence of base such as sodium hydride, alkoxide or DBU.

The former reaction is made, using a method of Matsumoto et al. [SYNTHESIS, 249–250 (1977)]. The latter reaction is made, using 2–3 moles of the compound III or 1.0–1.2 moles of the compound III' per mole of isocyano acetamide.

The reaction solvent used may be THF, dioxane or DMF. THF is preferable.

The base used may be preferably NaH; a mole of NaH is used per mole of the compound III or III'.

The reaction may be carried out in a range from room temperature to 80° C. and the preferable reaction temperature is 50° C.

Thus obtained compounds of the present invention may be separated and purified according to an ordinary method such as extraction, condensation, neutralization, filtration, recrystallization or column chromatography.

[Pharmacological Effects]

Next, pharmacological effects of the compounds of the present invention represented by the formula I will be described. The numbers of test compounds in experiment 1 correspond to compound numbers in Examples referred to hereinafter. Comparative compounds used were the following antidementia compounds.

Compound A: linopirdine[3,3-bis(4-pyridylmethyl)-1-phenylindolin-2-one]
Compound B: tacrine[9-amino-1,2,3,4-tetrahydroacridine]
Compound C: aricept [(R,S)-1-benzyl-4-(5,6-dimethoxy-1-indanon-2-yl)-methylpiperidine]

Experiment 1

Effects on Scopolamine-induced Amnesia (Through Oral Administration)

Male rats of the Strague Dawley strain at 8 weeks of age (260±2 g body weight) were used for evaluation through passive avoidance task. The apparatus of passive avoidance task comprises illuminated and dark chambers which are separated from each other by a wall with a door. Floors are constituted by grids made of stainless steel; only the grid in the dark chamber is furnished with wiring for electrification.

Effected on the first and second days of testing was preparative training; each rat was placed in the illuminated chamber and left for 3 minutes to habituate to the apparatus. On the third day of testing, the rats were individually placed in the illuminated chamber and after entering the dark chamber, the door was closed and the floor grid was electrified to deliver electric shock (100 V, 0.4 mA, a period of 0.8 sec). In order to induce amnesia, scopolamine hydrobromide (2 mg/kg) was intraperitoneally injected 20 minutes before the electric shock was delivered. Retention in memory on the electric shock was tested 24 hours later; more specifically, retention in passive avoidance was measured in terms of a time interval (latency) from placement of each rat in the illuminated chamber to its entry into the dark chamber. The latency over 300 seconds was recorded as 300 seconds. Respective test compounds were suspended in an aqueous solution of 1% carboxymethyl cellulose and orally administered at a dose of 0.01 or 1 mg/kg 60 minutes before the trial.

Antiamnesic effects of the test compounds were evaluated by inhibitory rate (%) which is calculated by the following formula:

$$\text{Inhibitory rate } (\%) = \frac{T\,(\text{Treatment} + SC) - T\,(\text{Placebo} + SC)}{T\,(\text{Placebo}) - T\,(\text{Placebo} + SC)} \times 100$$

wherein T stands for latency and SC, administration of scopolamine hydrobromide. Experimental results are shown in the following table in which, as to each of the test compounds, only the dose showing higher inhibitory rate was indicated.

TABLE 1

Effects on amnesia of rats induced by scopolamine

| Test compound | Dose (mg/kg, p.o.) | Inhibitory rate (%) |
| --- | --- | --- |
| compound 1 | 1 | 56.1* |
| compound 2 | 0.01 | 86.9* |
| compound 3 | 0.01 | 60.3* |
| compound 4 | 0.01 | 49.8* |
| compound 5 | 0.01 | 49.6* |
| compound 6 | 0.01 | 66.6* |
| compound 8 | 0.01 | 58.9** |
| compound 9 | 0.01 | 86.6** |
| compound 10 | 0.01 | 40.8* |
| compound 11 | 0.01 | 80.4** |
| compound 12 | 0.01 | 53.5* |
| compound 13 | 1 | 49.6* |
| compound 14 | 0.01 | 53.6* |
| compound 15 | 1 | 61.5* |
| compound 16 | 0.01 | 73.3* |
| compound 17 | 0.01 | 54.4* |
| compound 18 | 0.01 | 90.3** |
| compound 19 | 1 | 83.4** |
| compound 20 | 1 | 72.4** |
| compound 21 | 1 | 52.4* |
| compound 22 | 0.01 | 76.5** |
| compound 23 | 0.01 | 88.2** |
| compound 24 | 0.01 | 97.1** |
| compound 25 | 1 | 78.3* |
| compound 26 | 1 | 74.3** |
| compound 27 | 1 | 64.9** |
| compound 28 | 0.01 | 88.0** |
| compound 29 | 1 | 87.7** |
| compound 30 | 1 | 89.5** |
| compound 31 | 0.01 | 56.7* |
| compound 32 | 0.01 | 61.4* |
| compound 33 | 0.01 | 66.1** |
| compound A | 0.01 | 8.8 |
|  | 1 | 20.9 |
| compound B | 0.01 | 24.1 |
|  | 1 | 54.9** |
| compound C | 0.01 | 12.5 |
|  | 1 | 24.7 |

**p < 0.01,
*P < 0.05 (by Mann-Whitney U-test in comparison with scopolamine control group)

As is clear from the above results of Experiment 1, the compounds of the present invention exhibited greater antiamnesic effects than those of the known comparative compounds.

The compounds of the present invention represented by formula I are extremely advantageous in separating actions on the central and peripheral nerves and have no peripheral actions such as convulsion, salivation and diarrhea at a dose (0.001–10 mg/kg) showing antiamnesic effects on rat, and exhibit remarkable effects through oral administration. Therefore, they may be effective as cognitive enhancers for mammals including human.

The compounds of the present invention may be effective on diseases such as senile dementia, Alzheimer's disease, Parkinson's disease and other disorders in the central nervous system and can be used for prevention or treatment of these diseases.

Next, described are ways, forms and amounts of administration in application of the compounds of the present invention to mammals, especially human.

The compounds of the present invention may be administered orally or parenterally. In oral administration, the compounds may be in the form of tablets, coated tablets, powders, granules, capsules, microcapsules, syrups and the like; and in parenteral administration, in the appearance of suppositories and the like. In the preparation of these forms, pharmacologically acceptable excipient, binders, lubricants, disintegrators, suspensions, emulsifiers, antiseptics, stabilizers and dispersing agents, for example, lactose, sucrose, starch, dextrin, crystalline cellulose, kaolin, calcium carbonate, talc, magnesium stearate, distilled water and physiological saline solution may be used.

The dosage for humans may depend on the condition of the disease to be treated, the age and weight of the patient and the like. A daily dosage for an adult may be in the range from 0.1 to 50 mg and may be given in divided doses 1 to 3 times a day.

BEST MODE FOR CARRYING OUT THE INVENTION

The present invention is more specifically illustrated with reference to the following examples. It is to be, however, noted that the present invention is not limited to these.

EXAMPLE 1

5,5-bis(4-fluorobenzyl)imidazo[2,1-b]thiazol-6(5H)-one (Compound 1)

Sodium ethoxide prepared from 210 mg (9.0 mmol) of metallic sodium and dissolved in ethanol (10 ml) was added with, under ice cooling, 300 mg (1.4 mmol) of 2-amino-3-ethoxycarbonylmethylthiazoliumbromide and then with 1.15 ml (9.0 mmol) of p-fluorobenzylbromide at 0° C. and stirred at room temperature overnight. Then, the solvent was removed under reduced pressure and the residue was added with water and extracted several times with ethyl acetate. The extract was washed with saturated saline solution and dried over anhydrous magnesium sulphate. The solvent was removed under reduced pressure and the residue was separated by silica gel column chromatography (ethyl acetate: methanol=10:1) to obtain 852 mg (yield: 80.0%) of the titled compound as crystal. The obtained crystals were recrystallized from ethanol to obtain colorless crystals with melting point of more than 300° C.

NMR(CD$_3$OD-CDCl$_3$ (1:1)) δ: 3.23(2H, d, J=14 Hz), 3.43(2H, d, J=14 Hz), 6.66(1H, d, J=4 Hz), 6.8–6.9(4H, m), 6.9–7.1(4H, m) 7.28(1H, d, J=4 Hz) MS m/z: 356(M$^+$)

The following compounds were obtained from the corresponding starting materials and in a process similar to that in Example 1.

5,5-dibenzylimidazo[2,1-b]thiazol-6(5H)-one (Compound 2)

Melting point: >300° C. NMR(DMSO-d$_6$) δ: 3.69(2H, d, J=15 Hz), 3.74(2H, d, J=15 Hz), 7.27 (1H, d, J=4 Hz), 7.3–7.4 (4H, m), 7.5–7.6(6H, m), 8.44 (1H, d, J=4 Hz) MS m/z: 320 (M$^+$)

3,3-dibenzylimidazo[1,2-a]pyrimidin-2(3H)-one (Compound 3)

Melting point: >300° C. NMR(DMSO-d$_6$) δ: 3.42(4H, dd, J=14 Hz, J=16 Hz), 6.9–7.0(5H, m), 7.1–7.2(6H, m), 8.46 (1H, dd, J=3 Hz, J=5 Hz), 9.07(1H, dd, J=2 Hz, J=6 Hz) MS m/z: 315 (M$^+$)

5,5-bis(4-methylbenzyl)imidazo[2,1-b]thiazol-6 (5H)-one (Compound 4)

Melting point: >300° C. NMR(DMSO-d$_6$) δ: 2.20 (6H, s), 3.24 (2H, d, J=14 Hz), 3.36(2H, d, J=14 Hz), 6.84 (4H, d, J=8 Hz), 6.89 (1H, d, J=4 Hz), 6.97 (4H, d, J=8 Hz), 8.03(4H, d, J=4 Hz) MS m/z: 348 (M$^+$)

5,5-bis(4-cyanobenzyl)imidazo[2,1-b]thiazol-6(5H)-one (Compound 5)

Melting point: 264–267° C. NMR(CDCl$_3$) δ: 3.23(2H, d, J=14 Hz), 3.56(2H, d, J=14 Hz), 6.54 (1H, d, J=6 Hz), 7.02(1H, d, J=6 Hz), 7.15(4H, d, J=9 Hz), 7.51(4H, d, J=9 Hz) MS m/z: 370(M$^+$)

5,5-dibenzyl-2-methylimidazo[2,1-b]thiazol-6(5H)-one (Compound 6)

Melting point: >300° C. NMR(CD$_3$OD-CDCl$_3$ (1:1)) δ: 2.34(3H, d, J=1 Hz), 3.28(2H, d, J=13 Hz), 3.43(2H, d, J=13 Hz), 7.0–7.1(4H, m), 7.1–7.3(7H,m)
MS m/z: 334 (M$^+$)

5,5-bis(2-thienylmethyl)imidazo[2,1-b]thiazol-6 (5H)-one (Compound 7)

Melting point: 286° C. (decomp.) NMR(CDCl$_3$) δ: 3.43 (2H, d, J=15 Hz), 3.60(2H, d, J=15 Hz), 6.49(1H, d, J=5 Hz), 6.7–7.0(5H, m), 7.12(2H, dd, J=1 Hz, J=6 Hz) MS m/z: 332 (M$^+$)

3,3-bis(2-thienylmethyl)imidazo[1,2-a]pyrimidin-2 (3H)-one (Compound 8)

Melting point: 192° C. (decomp.) NMR(CD$_3$OD-CDCl$_3$ (1:1)) δ: 3.54 (2H, d, J=15 Hz), 3.76(2H, d, J=15 Hz), 6.7–6.9(5H, m), 7.11(2H, dd, J=1 Hz, J=5 Hz), 8.23(1H, dd, J=2 Hz, J=6 Hz), 8.62(1H, dd, J=2 Hz, J=4 Hz) MS m/z: 327 (M$^+$)

5,5-dibenzyl-2,3-dihydroimidazo[2,1-b]thiazol-6 (5H)-one (Compound 9)

Melting point: 233–236° C. NMR(CDCl$_3$) δ: 3.03(2H, d, J=14 Hz), 3.23(2H, t, J=7 Hz), 3.41(2H, d, J=14 Hz), 3.63(2H, t, J=7 Hz), 7.1–7.2 (4H, m), 7.2–7.3(6H, m) MS m/z: 322 (M$^+$)

2-hydroxy-3-(2-naphtylmethyl)imidazo[1,2-a]pyridin (Compound 10)

Melting point: 205° C. (decomp.) NMR(CD$_3$OD-CDCl$_3$ (1:1)) δ: 3.41(1H, d, J=15 Hz), 3.76(1H, d, J=15 Hz), 6.72(1H, t, J=7 Hz), 7.02(1H, d, J=9 Hz), 7.29(1H, d, J=9 Hz), 7.4–7.5(2H, m), 7.58(2H, brs), 7.6–7.9(4H, m) MS m/z: 274 (M$^+$)

spiro[imidazo[1,2-a]pyridin-2(3H)-one-3,2'-benzo[f]-indan] (Compound 11)

Melting point: 214° C. (decomp.) NMR(CD$_3$OD-CDCl$_3$ (1:1)) δ: 3.33(2H, d, J=16 Hz), 4.02(2H, d, J=16 Hz), 6.58(1H, t, J=7 Hz), 7.16(1H, d, J=7 Hz), 7.24(1H, d, J=9 Hz), 7.5–7.6(2H, m), 7.74(1H, t, J=8 Hz), 7.8–7.9(4H, m) MS m/z: 286(M$^+$)

3-benzylimidazo[1,2-a]pyridin-2(3H)-one (Compound 14)

Melting point: 182° C. (decomp.) NMR(CDCl$_3$) δ: 3.09 (1H, dd, J=8 Hz, J=15 Hz), 3.64 (1H, dd, J=4 Hz, J=15 Hz), 4.58(1H, dd, J=4 Hz, J=8 Hz), 6.47(1H, t, J=7 Hz), 7.0–7.1 (2H, m), 7.1–7.2 (2H, m), 7.3–7.4 (3H, m), 7.54 (1H, t, J=7 Hz) MS m/z: 224 (M$^+$)

3,3-di(2-butenyl)imidazo[1,2-a]pyrimidin-2(3H)-one (Compound 17)

Melting point: 149.5° C. (decomp.) NMR(CDCl$_3$) δ: 1.55(6H, d, J=6 Hz), 2.51(2H, dd, J=8 Hz, J=15 Hz), 2.76(2H, dd, J=8 Hz, J=15 Hz), 5.1–5.3(2H, m), 5.4–5.7 (2H, m), 6.69(1H, dd, J=5 Hz, J=6 Hz), 7.75(1H, dd, J=2 Hz, J=6 Hz), 8.7 (1H, dd, J=2 Hz, J=5 Hz) MS m/z: 243(M$^+$)

spiro[imidazo[1,2-a]pyridin-2(3H)-one-3,2'-(4'-fluoroindan)] (Compound 18)

Melting point: 148.0° C. (decomp.) NMR(CDCl$_3$) δ: 3.24 (2H, dd, J=18 Hz, J=22 Hz), 3.88 (2H, t, J=18 Hz) 6.55(1H, t, J=7 Hz), 7.01(1H, t, J=9 Hz), 7.10(1H, d, J=7 Hz), 7.2–7.3(3H, m), 7.63(1H, t, J=8 Hz) MS m/z: 254 (M$^+$)

spiro[imidazo[1,2-a]pyridin-2(3H)-one-3,2'-(5'-methoxyindan)] (Compound 19)

Melting point: 150.0–152.0° C. (decomp.) NMR(CDCl$_3$) δ: 3.08 (2H, dd, J=6 Hz, J=17 Hz), 3.8–4.0(5H, m), 6.49(1H, t, J=7 Hz), 6.8–6.9(2H, m), 7.1–7.3(3H, m), 7.60(1H, t, J=7 Hz) MS m/z: 266(M$^+$)

spiro[imidazo[1,2-a]pyridin-2(3H)-one-3,2'-(5'-iodo-indan)] (Compound 20)

Melting point: 167–171° C. NMR (CDCl$_3$) δ: 3.14 (2H, dd, J=6 Hz, J=17 Hz), 3.82 (2H, dd, J=17 Hz, J=18 Hz), 6.57 (1H, t, J=7 Hz), 7.08 (1H, d, J=8 Hz), 7.1–7.3 (2H, m), 7.6–7.7(3H, m) MS m/z: 362(M$^+$)

spiro[imidazo[1,2-a]pyridin-2(3H)-one-3,2'-(4'-cyanoindan)] (Compound 21)

Melting point: 247.7° C. (decomp.) NMR(CDCl$_3$) δ: 3.26(2H, dd, J=3 Hz, J=18 Hz), 3.93(2H, dd, J=6 Hz, J=18 Hz), 6.56(1H, t, J=7 Hz), 7.15(1H, d, J=7 Hz), 7.23(1H, d, J=9 Hz), 7.44(1H, d, J=8 Hz), 7.6–7.7(3H, m) MS m/z: 261(M$^+$)

spiro[imidazo[2,1-a]isoquinolin-2(3H)-one-3,2'-indan] (Compound 22)

Melting point: 201–203° C. NMR(CDCl$_3$) δ: 3.22 (2H, d, J=17 Hz), 3.91 (2H, d, J=17 Hz), 6.74 (1H, d, J=7 Hz), 6.89 (1H, d, J=7 Hz), 7.32 (4H, s), 7.6–7.7 (2H, m) 7.79(1H, t, J=7 Hz), 8.63(1H, d, J=8 Hz) MS m/z: 286(M$^+$)

spiro[imidazo[1,2-a]pyridin-2(3H)-one-3,2'-((1,2,5-thiadiazo)[4,5-c]indan)] (Compound 23)

Melting point: 86–88° C. NMR(CDCl$_3$—CD$_3$OD (1:1)) δ: 3.44(2H, d, J=18 Hz), 4.00(2H, d, J=18 Hz), 6.71 (1H, t, J=7 Hz), 7.2–7.4 (2H, m), 7.81 (1H, t, J=7 Hz) 7.97(2H, s) MS m/z: 294 (M$^+$)

spiro[imidazo[2,1-a]isoquinolin-2(3H)-one-3,2'-((1,2,5-thiadiazo)[4,5-c]indan)] (Compound 24)

Melting point: 271.5° C. (decomp.) NMR(CDCl$_3$) δ: 3.39(2H, d, J=16 Hz), 4.04(2H, brd, J=16 Hz), 6.77 (1H, d, J=7 Hz), 6.81(1H, d, J=7 Hz), 7.6–7.8 (2H, m), 7.82(1H, brt, J=8 Hz), 7.95(2H, brs), 8.65(1H, d, J=8 Hz) MS m/z: 344 (M$^+$)

spiro[imidazo[1,2-a]pyrimidin-2(3H)-one-3,2'-indan] (Compound 25)

Melting point: 195.5° C. (decomp.) NMR(CDCl$_3$) δ: 3.17(2H, d, J=17 Hz), 3.92(2H, d, J=17 Hz), 6.53(1H, dd, J=5 Hz, J=6 Hz), 7.44(1H, dd, J=2 Hz, J=6 Hz), 7.32(4H, s), 8.72(1H, dd, J=2 Hz, J=5 Hz) MS m/z: 237 (M$^+$)

spiro[imidazo[1,2-a]pyridin-2(3H)-one-3,2'-(5'-trifluoromethylindan)] (Compound 26)

Melting point: 176.5–179.5° C. NMR(CDCl$_3$) δ: 3.25 (2H, d, J=17 Hz), 3.92(2H, d, J=17 Hz), 6.57 (1H, t, J=7 Hz), 7.1–7.2(2H, m), 7.44(1H, d, J=8 Hz), 8.5–8.7(3H, m) MS m/z: 304 (M$^+$)

spiro[imidazo[1,2-a]pyridin-2(3H)-one-3,2'-benzo[e]-indan] (Compound 27)

Melting point: 256.0° C. (decomp.) NMR(CDCl$_3$) δ: 3.33(1H, d, J=17 Hz), 3.56(1H, d, J=17 Hz), 4.09(2H, t, J=17 Hz), 6.50(1H, t, J=7 Hz), 7.22(1H, d, J=9 Hz), 7.29 (1H, d, J=7 Hz), 7.42(1H, d, J=8 Hz), 7.5–7.7(4H, m), 7.83(1H, d, J=8 Hz), 7.92(1H, d, J=6 Hz) MS m/z: 286(M$^+$)

3,3-diarylimidazo[1,2-a]pyridin-2(3H)-one

Melting point: 64–66° C. NMR(CDCl$_3$) δ: 2.56(2H, dd, J=9 Hz, J=14 Hz), 2.86(2H, dd, J=6 Hz, J=14 Hz), 4.99(2H, dd, J=1 Hz, J=7 Hz), 5.40(2H, d, J=1 Hz), 5.4–5.6(2H, m), 6.67 (1H, t, J=7 Hz), 7.17 (1H, d, J=7 Hz), 7.52 (1H, d, J=7 Hz), 7.59 (1H, d, J=7 Hz) MS m/z: 214 (M$^+$)

3,3-bis(2-cyclohexenyl)imidazo[1,2-a]pyridin-2(3H)-one

Melting point: 245–247° C. NMR(CDCl$_3$) δ: 1.4–2.0 (12H, m), 2.9–3.1(2H, m), 5.29(1H, brd, J=10 Hz), 5.8–6.0 (3H, m), 6.62 (1H, t, J=7 Hz), 7.17 (1H, d, J=9 Hz) 7.5–7.7(2H, m)
MS m/z: 294 (M$^+$)

3,3-diarylimidazo[1,2-a]pyridin-2(3H)-one

Melting point: 64–66° C. NMR(CDCl$_3$) δ: 2.56(2H, dd, J=9 Hz, J=14 Hz), 2.86(2H, dd, J=6 Hz, J=14 Hz), 4.99(2H, dd, J=1 Hz, J=7 Hz), 5.04 (2H, d, J=1 Hz), 5.4–5.6(2H, m), 6.67 (1H, t, J=7 Hz), 7.17(1H, d, J=7 Hz), 7.52(1H, d, J=7 Hz), 7.59(1H, d, J=7 Hz) MS m/z: 214 (M$^+$)

spiro[imidazo[1,2-a]pyridin-2(3H)-one-3,2'-indan]

Melting point: 206° C. (decomp.) NMR(CDCl$_3$) δ: 3.16 (2H, d, J=16 Hz), 3.89(2H, d, J=16 Hz), 6.49(1H, t, J=7 Hz), 7.1–7.2 (2H, m), 7.2–7.3(4H, m), 7.61(1H, t, J=7 Hz) MS m/z: 236(M$^+$)

3,3-diaryl-8-benzyloxyimidazo[1,2-a]pyridin-2(3H)-one

Melting point: 160–162° C. NMR(CDCl$_3$) δ: 2.54(2H, dd, J=8 Hz, J=14 Hz), 2.86(2H, dd, J=6 Hz, J=14 Hz), 4.96(2H, dd, J=1 Hz, J=5 Hz), 5.01(2H, d, J=1 Hz) 5.29(2H, s), 5.4–5.6(2H, m), 6.53(1H, dd, J=7 Hz, J=8 Hz) 6.94 (1H, d, J=7 Hz), 7.16 (1H, d, J=8 Hz), 7.3–7.5 (5H, m) MS m/z: 320(M$^+$)

3,3-dibutylimidazo[1,2-a]pyridin-2(3H)-one

Melting point: 100.5–102° C. NMR(CDCl$_3$) δ: 0.6–0.9 (8H, m), 1.0–1.3(6H, m), 1.6–1.8(2H, m), 2.0–2.2(2H, m), 6.71(1H, t, J=7 Hz), 7.19(1H, d, J=7 Hz), 7.50(1H, d, J=7 Hz), 7.62(1H, t, J=7 Hz) MS m/z: 246(M$^+$)

3,3-di(2-cyclohexenyl)imidazo[1,2-a]pyridin-2(3H)-one

Melting point: 249.0° C. (decomp.) NMR (CDCl$_3$) δ: 1.4–2.0 (12H, m), 2.9–3.1 (2H, m), 5.2–5.3 (1H, m), 5.8–6.0 (3H, m), 6.62(1H, t, J=7 Hz), 7.17(1H, d, J=9 Hz), 7.5–7.7 (2H, m)
MS m/z: 297 (M$^+$)

3,3-diarylimidazo[2,1-a]isoquinolin-2(3H)-one

Melting point: 108–110° C. NMR(CDCl$_3$) δ: 2.62(2H, dd, J=8 Hz, J=14 Hz), 2.89(2H, dd, J=6 Hz, J=14 Hz), 4.9–5.1 (4H, m), 5.4–5.6(2H, m), 6.91(1H, d, J=7 Hz), 7.25 (1H, d, J=7 Hz), 7.6–7.7 (2H, m), 7.80 (1H, t, J=8 Hz), 8.57 (1H, d, J=8 Hz) MS m/z: 264 (M$^+$)

EXAMPLE 2

Spiro[imidazo[2,1-a]isoquinolin-2(3H)-one-3,1'-(3'-cyclopentene)] (Compound 28)

Under argon atmosphere, 1.0 g (3.8 mmol) of 3,3-diarylimidazo[2,1-a]isoquinolin-2 (3H)-one obtained in a process similar to that in Example 1 and dissolved in chloroform (80 ml) is added with 80 mg (0.24 mmol) of Grubbs reagent and refluxed under heating for 14 hours. The reaction mixture was allowed to cool and the solvent was removed under reduced pressure. The obtained residue was added with water and extracted with dichloromethan for several times. The extracted layers are combined and washed with saturated saline solution and dried over anhydrous magnesium sulphate. The solvent was removed under reduced pressure and the residue was separated and purified by silica gel column chromatography (ethyl acetate:methanol=10:1) to obtain 748 mg (yield: 83.5%) of the titled compound as pale brown crystals.

Melting point: 173.5° C. (decomp.) NMR(CDCl$_3$) δ: 2.70(2H, d, J=17 Hz), 3.30(2H, d, J=17 Hz), 5.92(2H, s), 6.89(1H, d, J=7 Hz), 7.33(1H, d, J=7 Hz), 7.6–7.8(2H, m) 7.79(1H, t, J=7 Hz), 8.60(1H, d, J=7 Hz) MS m/z: 236(M$^+$)

The following compounds were obtained from the corresponding starting materials and in a process similar to that in Example 2.

spiro[8-benzyloxyimidazo[1,2-a]pyridin-2(3H)-one-3,1'-(3'-cyclopentene)] (Compound 29)

Melting point: 178.5–180.5° C. NMR(CDCl$_3$) 67 : 2.64 (2H, d, J=16 Hz), 3.29(2H, d, J=16 Hz), 5.30(2H, s), 5.88(2H, s), 6.49(1H, dd, J=6 Hz, J=8 Hz), 6.94 (1H, dd, J=6 Hz, J=8 Hz), 6.94(1H, d, J=8 Hz), 7.2–7.5(5H, m) MS m/z: 292(M$^+$)

EXAMPLE 3

3,3-dipropyl-5,6,7,8-tetrahydroimidazo[1,2-a]pyridin-2(3H)-one (Compound 15)

300 Mg (1.4 mmol) of 3,3-diarylimidazo[1,2-a]pyridin-2 (3H)-one prepared in the same way as that of Example 1 and dissolved in 30 ml of ethanol was added with 100 mg of 10% palladium carbon and underwent catalytic reduction at room temperature for overnight under hydrogen atmosphere. Insolubles are filtered out and the solvent was removed from the filtrate under reduced pressure. The residue was separated by silica gel column chromatography (hexane:ethyl acetate=10:1) to obtain 281 mg (yield: 90.3%) of the titled compound as crystal. The obtained crystals were recrystallized from hexane-ethyl acetate (10:1) to obtain white crystal with the melting point of 98.5–101° C.

NMR (CDCl$_3$) δ: 0.86(6H, t, J=7 Hz), 0.9–1.1(2H, m), 1.1–1.2(2H, m), 1.4–1.6(2H, m), 1.7–2.0(6H, m), 2.79(2H, t, J=6 Hz), 3.19(2H, t, J=6 Hz) MS m/z: 222 (M$^+$)

The following compounds were obtained from the corresponding starting materials and in a process similar to that in Example 3.

3,3-dicyclohexyl-5,6,7,8-tetrahydroimidazo[1,2-a]pyridin-2(3H)-one (Compound 12)

Melting point: 218–220° C. NMR(CDCl$_3$) δ: 0.9–1.4(8H, m), 1.5–2.0(18H, m), 2.79(2H, t, J=6 Hz), 3.30(2H, t, J=6 Hz) MS m/z: 302 (M$^+$)

3,3-dibutyl-5,6,7,8-tetrahydroimidazo[1,2-a]pyridin-2(3H)-one (Compound 13)

Melting point: 35–40° C. NMR(CDCl$_3$) δ: 0.88(6H, t, J=7 Hz), 0.9–1.4(8H, m), 1.6–2.2(8H, m), 3.2–3.4(4H, m) MS m/z: 250 (M$^+$)

spiro[7,8,9,10-tetrahydroimidazo[2,1-a]isoquinolin-2(3H)-one-3,1'-cyclopentane] (Compound 30)

Melting point: 270.5° C. (decomp.) NMR (CDCl$_3$) δ: 1.8–2.2 (10H, m), 2.3–2.5 (2H, m), 2.6–2.8 (4H, m), 6.44 (1H, d, J=7 Hz), 7.35(1H, d, J=7 Hz) MS m/z: 242(M$^+$)

spiro[imidazo[2,1-a]isoquinolin-2(3H)-one-3,1'-cyclopentane] (Compound 31)

Melting point: 164.5–167.5° C. NMR(CDCl$_3$) δ: 1.8–2.3 (6H, m), 2.4–2.6(2H, m), 6.94(1H, d, J=7 Hz), 7.33(1H, d, J=7 Hz), 7.6–7.7 (2H, m), 7.79(1H, t, J=6 Hz) 8.60(1H, d, J=8 Hz) MS m/z: 238 (M$^+$)

spiro[5,6,7,8-tetrahydroimidazo[1,2-a]pyridin-2(3H)-one-3,2'-benzo[f]indan] (Compound 32)

Melting point: 252.5° C. (decomp.) NMR (CDCl$_3$-CD$_3$OD (1:1)) δ: 1.9–2.1 (4H, m), 3.0–3.2 (4H, m) 3.50(2H, d, J=18 Hz), 3.79(2H, d, J=18 Hz), 7.4–7.5(2H, m), 7.75(2H, s), 7.8–7.9(2H, m) MS m/z: 290(M$^+$)

spiro[5,6,7,8-tetrahydroimidazo[1,2-a]pyridin-2(3H)-one-3,2'-indan] (Compound 33)

Melting point: 276.5° C. (decomp.) NMR (CDCl$_3$-CD$_3$OD (1:1)) δ: 1.9–2.1 (4H, m), 3.0–3.3 (4H, m) 3.45(2H, d, J=17 Hz), 3.66(2H, d, J=17 Hz), 7.30(4H, s) MS m/z: 240(M$^+$)

EXAMPLE 4

4,4-dibenzyl-1-methyl-5-oxo-4,5-dihydroimidazol (Compound 16)

1.13 g (10 mmol) of isocyano ethyl acetate dissolved in 5 ml of methanol was added with methylamine (40% solution in methanol, 5 ml) and the reaction was made at room temperature for 2 hours in a sealed tube. The solvent was removed under reduced pressure from the reaction mixture and the residue was purified by silica gel column chromatography (ethyl acetate:hexane:ethanol=8:2:1) to obtain 860 mg (yield: 88%) of acetamide.

530 Mg (13.2 mmol) of 60% of sodium hydride suspended in 10 ml of THF was added with 590 mg (6 mmol) of the above-mentioned acetamide and 1.4 ml (12 mmol) of benzyl bromide dissolved in 10 ml of THF and heated at 50° C. for two hours. The reaction mixture was added with water, extracted twice by 100 ml of ethyl acetate, washed with water and dried over magnesium sulphate. The solvent was removed and the residue was purified by silica gel column chromatography (ethyl acetate:hexane=1:1) to obtain 1.22 g (yield: 73%) of the titled compound.

Melting point: 125–126° C. NMR(CDCl$_3$): 2.54(3H, s), 3.11(2H, d, J=13 Hz), 3.19(3H, d, J=13 Hz), 7.08(1H, s), 7.1–7.2(10H, m) MS m/z: 278 (M$^+$)

CAPABILITY OF EXPLOITATION IN INDUSTRY

The compounds according to the present invention are extremely advantageous in separating actions on the central and peripheral nerves and exhibit remarkable antiamnesic effect by administration to rats, and therefore is applicable to improvement in cerebral function of mammals including humans and prevention and treatment of disorders in the central nervous system such as senile dementia, Alzheimer's disease and Parkinson's disease.

The invention claimed is:
1. A heterocyclic compound represented by formula I:

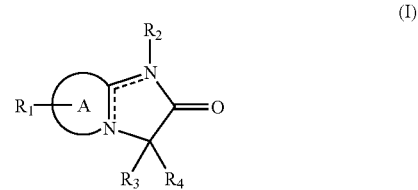

wherein

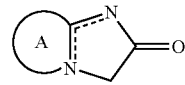

represents

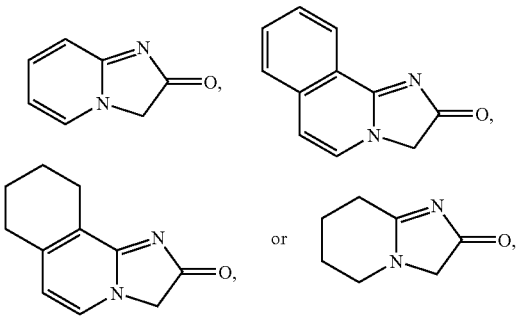

wherein:
R$_1$ represents hydrogen atom, C$_1$–C$_6$ alkyl or benzyloxy;
R$_2$ represents nil;
R$_3$ and R$_4$ together form:

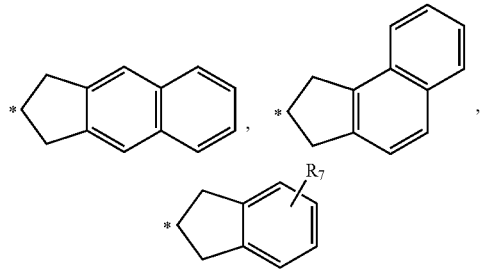

(wherein R$_7$ represents hydrogen atom, halogen atom, C$_1$–C$_6$ alkoxy, cyano or trifluoromethyl),

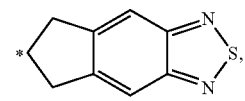

cyclopentene or cyclopentane, provided that, when

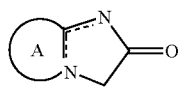

represents

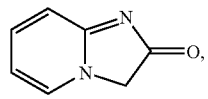

$R_3$ is coupled with $R_4$ into:

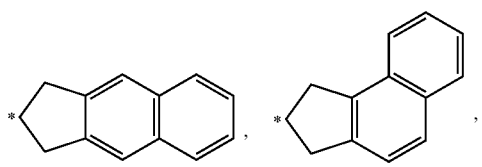

(wherein $R_8$ represents halogen atom, $C_1$–$C_6$ alkoxy, cyano or trifluoromethyl),

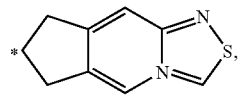

cyclopentene or cyclopentane;

where * indicates a permitted point of attachment of said ring to the position on the formula I ring to which $R^3$ and $R^4$ bind.

2. The compound of claim 1, wherein $R_1$ represents a hydrogen atom.

3. The compound of claim 1, wherein $R_1$ represents $C_{1-6}$ alkyl.

4. The compound of claim 1, wherein $R_1$ represents benzyloxy.

5. The compound of claim 1, wherein $R_3$ is coupled with $R_4$ into:

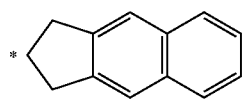

6. The compound of claim 1, wherein $R_3$ is coupled with $R_4$ into:

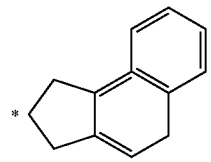

7. The compound of claim 1, wherein $R_3$ is coupled with $R_4$ into:

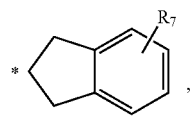

wherein $R_7$ represents halogen atom, $C_1$–$C_6$ alkoxy, cyano or trifluoromethyl.

8. The compound of claim 1, wherein $R_3$ is coupled with $R_4$ into:

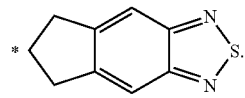

9. The compound of claim 1, wherein $R_3$ is coupled with $R_4$ into cyclopentene.

10. The compound of claim 1, wherein $R_3$ is coupled with $R_4$ into cyclopentane.

11. The compound according to claim 1, wherein $R_3$ is coupled with $R_4$ into indan which may be substituted with halogen.

12. The compound according to claim 1, which is:
spiro[imidazo[1,2-a]pyridin-2(3H)-one-3,2'-benzo[f]indan],
spiro[imidazo[1,2-a]pyridin-2(3H)-one-3,2'-(4'-fluoroindan)],
spiro[imidazo[1,2-a]pyridin-2(3H)-one-3,2'-((1,2,5-thiadiazo)[4,5-c]indan)],
spiro[5,6,7,8-tetrahydroimidazo[1,2-a]pyridin-2(3H)-one-3,2'-benzo[f]-indan],
spiro[5,6,7,8-tetrahydroimidazo[1,2-a]-pyridin-2(3H)-one-3,2'-indan],
spiro[imidazo[2,1-a]-isoquinolin-2(3H)-one-3,2'-indan],
spiro[imidazo[2,1-a]-isoquinolin-2(3H)-one-3,2'-((1,2,5-thiadiazo)[4,5-c]-indan)], or
spiro[imidazo[2,1-a]isoquinolin-2(3H)-one-3,1'-(3'-cyclopentene)].

13. A pharmaceutical composition containing an effective amount of at least one of compound according to claim 1 and at least one pharmaceutically acceptable diluent or carrier.

14. A composition comprising an amount of at least one compound of claim 1 effective to enhance cognition when administered to a subject in need thereof.

15. A method for enhancing cognition, comprising:
administering to a subject in need thereof an effective amount of the compound of claim 1.

* * * * *